United States Patent
Jerussi et al.

(10) Patent No.: US 6,506,753 B2
(45) Date of Patent: Jan. 14, 2003

(54) METHODS OF MAKING AND USING N-DESMETHYLZOPICLONE

(75) Inventors: Thomas P. Jerussi, Framingham, MA (US); Chrisantha H. Senanayake, Shrewsbury, MA (US); Paul D. Rubin, Sudbury, MA (US); Yaping Hong, Framingham, MA (US); Roger A. Bakale, Shrewsbury, MA (US); Tingjian Xiang, Thousand Oaks, CA (US); Fran A. McConville, Grafton, MA (US)

(73) Assignee: Sepracor, Inc., Marlborough, MA (US)

( * ) Notice: Subject to any disclaimer, the term of this patent is extended or adjusted under 35 U.S.C. 154(b) by 0 days.

(21) Appl. No.: 09/877,103

(22) Filed: Jun. 11, 2001

(65) Prior Publication Data

US 2002/0019398 A1 Feb. 14, 2002

Related U.S. Application Data

(62) Division of application No. 09/548,607, filed on Apr. 13, 2000, now Pat. No. 6,339,086.
(60) Provisional application No. 60/134,239, filed on May 14, 1999, and provisional application No. 60/135,037, filed on May 20, 1999.

(51) Int. Cl.$^7$ ............................................. A61K 31/50
(52) U.S. Cl. ..................................................... 514/249
(58) Field of Search ........................................... 514/249

(56) References Cited

U.S. PATENT DOCUMENTS

| | | | |
|---|---|---|---|
| 3,862,149 A | | 1/1975 | Cotrel et al. |
| 4,220,646 A | | 9/1980 | Cotrel et al. |
| 5,786,357 A | * | 7/1998 | Young et al. ............... 514/249 |
| 6,339,086 B1 | * | 1/2002 | Jerussi et al. ............... 514/249 |

FOREIGN PATENT DOCUMENTS

| WO | 93/10787 | 6/1993 |
|---|---|---|
| WO | 93/10788 | 6/1993 |

OTHER PUBLICATIONS

Brun, J.P., *Pharm. Biochem. Behav.* 29:831–832 (1988).
Castello, R.A., and Mattocks, A.M., *J. Phram. Sci.* 51(2):106–108 (1962).
Goa, K.L. and Heel, R.C., *Drugs*, (Abstr.) 32:48–65 (1986).
*Goodman & Gilman's The Pharmacological Basis of therapeutics*, Hardman, J.G., et al., eds. p. 142, 365 (9$^{th}$ ed., 1996).
*Handbook* of Pharmaceutical Excipients, 2$^{nd}$ ed., Wade and Willer eds., pp. 257–259 (1994).
Julou, L., et al., *Pharmacol. Biochem. Behav.* 23:653–659 (1985).
Meldrum, B.S., *Brit, J. Clin. Pharm.* 27(suppl. 1):3S–11S (1989).
Olofson, R.A. and Martz, T.J., *J. Org. Chem.*, 49:2081 (1984).
Sato, Katsuhiko, et al., *Pharmacologic Studies of Central Actions of Zopiclone. Influence on Brain Monoamines in Rats Under Stressful Condition*, (Abstr.), Tokyo Ika Daigaku Zasshi, 1985, vol. 43(1), pp. 45–51.
Turner, W., et al., A., *J. Med. Chem.* 20(8):1065–1068 (1977).
Verma, A. and Snyder, S.H., *Ann. Rev. Pharamcol. Toxicol.* 29:307–22 (1989).

* cited by examiner

Primary Examiner—William R. A. Jarvis
Assistant Examiner—Vickie Kim
(74) Attorney, Agent, or Firm—Pennie & Edmonds LLP

(57) ABSTRACT

The invention is directed to compositions comprising, and methods of using, racemic N-desmethylzopiclone, optically pure (+)-N-desmethylzopiclone, and optically pure (−)-N-desmethylzopiclone in the treatment and prevention of diseases and conditions in mammals. The invention is further directed to novel methods of preparing N-desmethylzopiclone, optically pure (+)-N-desmethylzopiclone, and optically pure (−)-N-desmethylzopiclone.

5 Claims, No Drawings

METHODS OF MAKING AND USING N-DESMETHYLZOPICLONE

This application is divisional of Ser. No. 09/548,607 filed Apr. 13, 2000, now patented U.S. Pat. No. 6,339,086 which claims benefit of Ser. No. 60/134,239 filed May 4, 1999 and claims benefit of Ser. No. 60/135,037 filed May 20, 1999.

FIELD OF THE INVENTION

The invention relates to compositions and methods for the treatment and prevention of anxiety, convulsive disorders, and other disorders.

BACKGROUND OF THE INVENTION

Zopiclone, chemically named (±)-6-(5-chloro-2-pyridinyl)-6,7-dihydro-7-oxo-5H-pyrrolo-[3,4b]pyrazin-5-yl-4-methylpiperazine-1-carboxylate, is a non-benzodiazepine hypnotic which has the following structure:

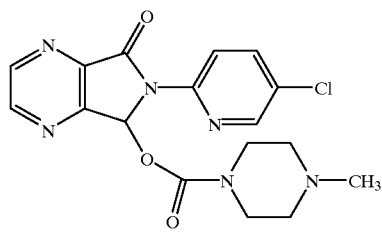

Zopiclone and some of its uses are described by U.S. Pat. Nos. 3,862,149 and 4,220,646. Uses of the optically pure (+) and (−) enantiomers of the drug (i.e., (+)-zopiclone and (−)-zopiclone) are described by U.S. Pat. No. 5,786,357 and WO 93/10788, respectively.

Zopiclone binds at or near benzodiazepine receptor complexes. Goa, K. L. and Heel, R. C. *Drugs*, 32:48–65 (1986). These complexes are located both within the central nervous system and peripherally (e.g., in the endocrine system), and contain macromolecular complexes which comprise benzodiazepine and GABA binding sites. Verma, A. and Snyder, S. H., *Annu. Rev. Pharmacol. Toxicol.* 29:307–22 (1989). Benzodiazepine receptor complexes are further associated with, and interact with, membrane channels for chloride ion transport. Upon binding to a benzodiazepine receptor complex, zopiclone is believed to allosterically modulate the activity of the complex by increasing trans-membrane conductance of chloride ions. This stabilizes neuronal membrane potentials and dampens excitatory input. See Meldrum, B. S., *Brit. J. Clin. Pharm.* 27(suppl. 1):3S–11S (1989); *Goodman & Gilman's The Pharmacological Basis of Therapeutics*, Hardman, J. G., et al., eds. p. 365 (9th ed., 1996).

Although chemically unrelated to the benzodiazepines, zopiclone possesses a spectrum of activity analogous to that of the benzodiazepines. Goa, K.L. and Heel, R. C. *Drugs*, 32:48–65, (1986). Zopiclone and its optically pure enantiomers are reportedly useful in the treatment of diseases and conditions including, but not limited to, epilepsy, anxiety, aggressive behavior, muscle tension, behavioral disorders, depression, schizophrenia, and endocrine disorders. See, e.g., WO 93/10787. Racemic zopiclone has been used to improve sleep in adults and geriatric patients with several types of sleep disorders including situational, transient primary and secondary insomnia. See, e.g., Brun, J. P., *Pharm. Biochem. Behav.* 29:831–832 (1988).

Some compounds which bind at benzodiazepine receptors can also have affinity for muscarinic receptors such as acetylcholine receptors. Julou, L., et al., *Pharmacol. Biochem. Behav.* 23:653–659 (1985). Consequently, administration of such compounds can result in adverse effects caused by muscarinic agonists and antagonists. Such adverse effects include, but are not limited to, drymouth, thirst, slowing and acceleration of the heart, dilated pupils, blurred vision, restlessness, fatigue, headache, hallucinations and delirium. *Goodman & Gilman's The Pharmacological Basis of Therapeutics*, Hardman, J. G., et al., eds. p. 142 (9th ed., 1996).

The metabolism of zopiclone is rapid and complex. When administered orally to healthy humans, the racemic drug is extensively metabolized by at least three major pathways, as shown below in Scheme 1.

Scheme 1

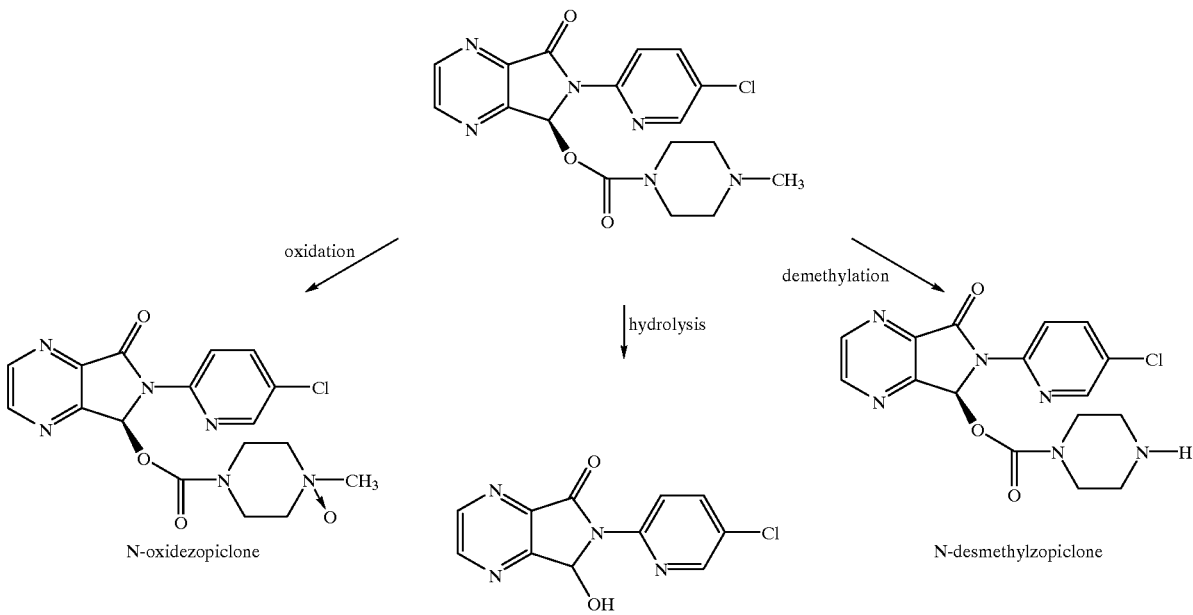

Metabolic pathways include oxidation, hydrolysis, and demethylation. An oxidation pathway produces N-oxidezopiclone, a metabolite which is reportedly less active than zopiclone and reportedly accounts for 11% of an oral dose of racemic zopiclone. A hydrolysis pathway produces an alcohol which is reportedly biologically inactive. A demethylation metabolic pathway produces N-desmethylzopiclone, a metabolite which reportedly accounts for 15% of an oral dose of racemic zopiclone, and which is also reportedly inactive. Goa, K. L. and Heel, R. C. Drugs, 32:48–65, (1986). Additional metabolites are formed from each of the three pathways shown in Scheme 1.

The full pharmacological activity of zopiclone is reportedly due to the drug itself and the N-oxide metabolite (i.e., N-oxidezopiclone). Id. Unfortunately, the single-dose elimination half-lives of both of these compounds after administration of racemic zopiclone range from only about 3.5 to about 6 hours, which limits the usefulness of zopiclone in the treatment of a wide number of disorders. For example, the rapid elimination of zopiclone and N-oxidezopiclone limits their usefulness in long-term anxiolytic treatment. The single-dose elimination half-life of the reportedly inactive N-desmethyl-zopiclone metabolite (herein referred to as "N-desmethylzopiclone") after administration of racemic zopiclone is between about 7 and about 11 hours in healthy subjects. Id.

Racemic zopiclone possesses further disadvantages, in particular, it causes adverse side effects which include, but are not limited to, the development of a bitter taste due to salivary secretion of the drug, dry mouth, heart palpitations, drowsiness, morning tiredness, headache, dizziness, impairment of psychomotor skills and related effects. A compound is thus desired for the treatment or prevention of various disorders which does not possesses disadvantages associated with racemic zopiclone.

SUMMARY OF THE INVENTION

The invention is directed to compositions comprising, and methods of using, racemic N-desmethylzopiclone ((±)-N-desmethylzopiclone), optically pure (+)-N-desmethylzopiclone, and optically pure (−)-N-desmethylzopiclone in the treatment and prevention of diseases and conditions in mammals.

One embodiment of the invention encompasses a method of treating or preventing anxiety in a patient which comprises administering to a patient in need of such treatment or prevention a therapeutically effective amount of N-desmethylzopiclone or a pharmaceutically acceptable salt, solvate, hydrate, or clathrate thereof. One method of this embodiment is the treatment or prevention of acute anxiety. Another method of this embodiment is the treatment or prevention of chronic anxiety. Yet another method of this embodiment is the treatment or prevention of general anxiety disorder. In a preferred method of this embodiment, N-desmethylzopiclone is (+)-N-desmethylzopiclone substantially free of its (−) enantiomer.

Another embodiment of the invention encompasses a method of treating or preventing a convulsive state in a patient which comprises administering to a patient in need of such treatment or prevention a therapeutically effective amount of N-desmethylzopiclone or a pharmaceutically acceptable salt, solvate, hydrate, or clathrate thereof. A particular method of this embodiment is the treatment or prevention of epilepsy or epileptic seizures. In a preferred method of this embodiment, N-desmethylzopiclone is (+)-N-desmethylzopiclone substantially free of its (−) enantiomer.

Yet another embodiment of the invention encompasses a method of treating or preventing an affective disorder in a patient which comprises administering to a patient in need of such treatment or prevention a therapeutically effective amount of N-desmethylzopiclone or a pharmaceutically acceptable salt, solvate, hydrate, or clathrate thereof. A particular method of this embodiment is the treatment or prevention of depression. Another method of this embodiment is the treatment or prevention of attention deficit disorder or attention deficit disorder with hyperactivity. In a preferred method of this embodiment, N-desmethylzopiclone is (+)-N-desmethylzopiclone substantially free of its (−) enantiomer.

A further embodiment of the invention encompasses a method of treating or preventing a sleep disorder in a patient which comprises administering to a patient in need of such treatment or prevention a therapeutically effective amount of N-desmethylzopiclone or a pharmaceutically acceptable salt, solvate, hydrate, or clathrate thereof. A particular method of this embodiment is the treatment or prevention of insomnia. In a preferred method of this embodiment, N-desmethylzopiclone is (+)-N-desmethylzopiclone substantially free of its (−) enantiomer.

Another embodiment of the invention encompasses a method of treating or preventing aggressive behavior in a patient which comprises administering to a patient in need of such treatment or prevention a therapeutically effective amount of N-desmethylzopiclone or a pharmaceutically acceptable salt, solvate, hydrate, or clathrate thereof. In a preferred method of this embodiment, N-desmethylzopiclone is (+)-N-desmethylzopiclone substantially free of its (−) enantiomer.

Still another embodiment of the invention encompasses a method of treating or preventing spasticity or acute muscle spasm spasticity in a patient which comprises administering to a patient in need of such treatment or prevention a therapeutically effective amount of N-desmethylzopiclone or a pharmaceutically acceptable salt, solvate, hydrate, or clathrate thereof. In a preferred method of this embodiment, N-desmethylzopiclone is (+)-N-desmethylzopiclone substantially free of its (−) enantiomer.

Yet another embodiment of the invention encompasses a method of treating or preventing a behavioral disorder in a patient which comprises administering to a patient in need of such treatment or prevention a therapeutically effective amount of N-desmethylzopiclone or a pharmaceutically acceptable salt, solvate, hydrate, or clathrate thereof. In a preferred method of this embodiment, N-desmethylzopiclone is (+)-N-desmethylzopiclone substantially free of its (−) enantiomer.

Still another embodiment of the invention encompasses a method of treating a schizophrenic disorder in a patient which comprises administering to a patient in need of such treatment or prevention a therapeutically effective amount of N-desmethylzopiclone or a pharmaceutically acceptable salt, solvate, hydrate, or clathrate thereof. In a preferred method of this embodiment, N-desmethylzopiclone is (+)-N-desmethylzopiclone substantially free of its (−) enantiomer.

Still another embodiment of the invention encompasses a method of treating or preventing a disease or condition associated with abnormal plasma hormone levels in a patient which comprises administering to a patient in need of such treatment or prevention a therapeutically effective amount of N-desmethylzopiclone or a pharmaceutically acceptable salt, solvate, hydrate, or clathrate thereof. In a particular method of this embodiment, the disorder is an endocrine disorder. In a preferred method of this embodiment, N-desmethylzopiclone is (+)-N-desmethylzopiclone substantially free of its (−) enantiomer.

Still another embodiment of the invention encompasses a method of treating alcohol or drug addiction in a patient which comprises administering to a patient in need of such treatment a therapeutically effective amount of N-desmethylzopiclone or a pharmaceutically acceptable salt, solvate, hydrate, or clathrate thereof. In a preferred method of this embodiment, N-desmethylzopiclone is (+)-N-desmethylzopiclone substantially free of its (−) enantiomer.

Still another embodiment of the invention encompasses a method of treating or preventing drug withdrawal, alcohol withdrawal, symptoms of drug withdrawal, or symptoms of alcohol withdrawal in a patient which comprises administering to a patient in need of such treatment a therapeutically effective amount of N-desmethylzopiclone or a pharmaceutically acceptable salt, solvate, hydrate, or clathrate thereof. Examples of such symptoms are disclosed herein. In a preferred method of this embodiment, N-desmethylzopiclone is (+)-N-desmethylzopiclone substantially free of its (−) enantiomer.

Patients who may receive the therapeutic or prophylactic benefits of the methods of the invention include those suffering from the diseases or conditions described above, as well as patients suffering from cancer, patients currently being treated with a muscarinic antagonist or a muscarinic agonist, and patients who are susceptible to adverse effects associated with racemic zopiclone.

A further embodiment of the invention encompasses pharmaceutical compositions comprising N-desmethylzopiclone, or a pharmaceutically acceptable salt, solvate, hydrate, or clathrate thereof. In preferred pharmaceutical compositions, N-desmethylzopiclone is (+)-N-desmethylzopiclone substantially free of its (−) enantiomer. Typical pharmaceutical compositions of the invention will comprise N-desmethylzopiclone and a pharmaceutically acceptable carrier. In one embodiment, the pharmaceutical compositions of the present invention are free of lactose (lactose-free), or other mono- or disaccharides. In another alternative embodiment, pharmaceutical compositions of the invention are anhydrous or anhydrous and lactose-free.

Also encompassed by the invention are single unit dosage forms of racemic and optically pure enantiomers of N-desmethylzopiclone, or pharmaceutically acceptable salts, solvates, hydrate, or clathrates thereof. Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration. Preferred single unit dosage forms of racemic and optically pure (+)- or (−)-N-desmethylzopiclone are suitable for oral administration. Most preferred single unit dosage forms of racemic and optically pure (+)- or (−)-N-desmethylzopiclone are tablets, capsules and caplets.

Another embodiment of the invention encompasses methods of preparing optically pure enantiomers of N-desmethylzopiclone. One method comprises treating an optically pure enantiomer of zopiclone with 1-chloroethyl chloroformate. Another method comprises treating an optically pure enantiomer of zopiclone with an azodicarboxylate, and hydrolyzing the resulting product under mild conditions. A preferred azodicarboxylate is diethyl azodicarboxylate. Yet another method of this embodiment comprises resolution of racemic desmethylzopiclone using L-N-benzyloxycarbonyl phenylalanine (L-ZPA) as a resolution reagent.

DETAILED DESCRIPTION OF THE INVENTION

The invention relates to the synthesis, use, and pharmaceutical compositions of N-desmethylzopiclone which, until now, was believed to possess no pharmacological activity. The invention further relates to the synthesis and use of optically pure (+)-N-desmethylzopiclone and optically pure (−)-N-desmethylzopiclone. A general aspect of the invention encompasses the use of (±)-N-desmethylzopiclone or optically pure enantiomers of N-desmethylzopiclone to treat or prevent diseases and conditions which are affected by the modulation of one or more central or peripheral benzodiazepine receptors.

Surprisingly, N-desmethylzopiclone, which has been reported to be pharmacologically inactive, is in fact a benzodiazepine receptor agonist. In addition, racemic and optically pure N-desmethylzopiclone only weakly antagonize muscarinic receptors. Thus, racemic N-desmethylzopiclone or an optically pure enantiomer of N-desmethylzopiclone may be used in the treatment or prevention of a disease or condition which is affected by the modulation of one or more benzodiazepine receptors. Further, racemic and optically pure enantiomers of N-desmethylzopiclone may be used in the treatment or prevention of such diseases and conditions while avoiding long single-dose elimination half-life and adverse effects associated with racemic zopiclone. Further still, racemic and optically pure enantiomers of N-desmethylzopiclone may be used in the treatment or prevention of such diseases and conditions while avoiding adverse effects associated with muscarinic receptor antagonists.

As used herein, the terms "mammal" and "patient" are used interchangeably, and include human.

The term "substantially free of its (−) enantiomer," as used herein, means that the composition contains a significantly greater proportion of the (+) enantiomer of N-desmethylzopiclone in relation to the (−) enantiomer of N-desmethylzopiclone. In a preferred embodiment of the present invention the term "substantially free of its (−) enantiomer," as used herein, means that the composition contains at least about 90% by weight of (+)-N-desmethylzopiclone and about 10% by weight or less of (−)-N-desmethylzopiclone. In a more preferred embodiment of the present invention, the term "substantially free of its (−) enantiomer," as used herein, means that the composition contains at least about 95% by weight of (+)-N-desmethylzopiclone and about 5% by weight or less of (−) N-desmethylzopiclone. In the most preferred embodiment, the term "substantially free of its (−) enantiomer," as used herein, means that the composition contains at least about 99% by weight of (+)-N-desmethylzopiclone and about 1% or less of (−)-N-desmethylzopiclone. In another preferred embodiment, the term "substantially free of its (−) enantiomer," as used herein, means that the composition contains nearly 100% by weight of the (+) isomer of N-desmethylzopiclone. The above percentages are based on the total amount of N-desmethylzopiclone present in the composition. The terms "substantially optically pure (+)-N-desmethylzopiclone," "optically pure (+)-N-desmethylzopiclone" and "(+) isomer of N-desmethylzopiclone" are also encompassed by the above described amounts.

The term "substantially free of its (+) enantiomer," as used herein, means that the composition contains a significantly greater proportion of the (−) enantiomer of N-desmethylzopiclone in relation to the (+) enantiomer of N-desmethylzopiclone. In a preferred embodiment of the present invention the term "substantially free of its (+) enantiomer," as used herein, means that the composition contains at least about 90% by weight of (−)-N-desmethylzopiclone and about 10% by weight or less of (+)-N-desmethylzopiclone. In a more preferred embodiment of the present invention the term "substantially free of its (+) enantiomer," as used herein, means that the composition contains at least about 95% by weight of (−)-N-desmethylzopiclone and about 5% by weight or less of (+)-N-desmethylzopiclone. In the most preferred embodiment, the term "substantially free of its (+) enantiomer," as used herein, means that the composition contains at least about 99% by weight of (−)-N-desmethylzopiclone and about 1% or less of (+)-N-desmethylzopiclone. In another preferred embodiment, the term "substantially free of its (+) enantiomer," as used herein, means that the composition contains nearly 100% by weight of the (−) isomer of N-desmethylzopiclone. The above percentages are based on the total amount of N-desmethylzopiclone present in the composition. The terms "substantially optically pure (−)-N-desmethylzopiclone," "optically pure (−)-N-desmethylzopiclone" and "(−) isomer of N-desmethylzopiclone" are also encompassed by the above described amounts.

As used herein, the term "pharmaceutically acceptable salt" refers to salts prepared from pharmaceutically acceptable non-toxic acids, including inorganic acids and organic acids. Suitable non-toxic acids include inorganic and organic acids such as acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. Particularly preferred are hydrochloric, hydrobromic, phosphoric, and sulfuric acids, and most particularly preferred is the hydrochloride salt.

As used herein, the term "benzodiazepine receptor agonist" means a compound that mimics the in vitro binding activity of a benzodiazepine (e.g., diazepam) to central or peripheral benzodiazepine receptors. As used herein, a benzodiazepine receptor agonist may exhibit full or partial agonistic effects as defined by *Goodman & Gilman's The Pharmacological Basis of Therapeutics,* Hardman, J. G., et al., eds. p. 364 (9$^{th}$ ed., 1996). Simply because a compound is referred to herein as a "benzodiazepine receptor agonist," however, does not imply that it exhibits a mechanism of action, a site of action, or an induced receptor conformational change identical to that of a benzodiazepine.

As used herein, the terms "diseases and conditions which are affected by the modulation of one or more central or peripheral benzodiazepine receptors," "diseases and conditions which are affected by the modulation of one or more benzodiazepine receptors," and "disease or condition affected by the modulation of a benzodiazepine receptor" mean a disease or condition that has at least one symptom which is mitigated or alleviated by allosteric binding of a compound to benzodiazepine receptors. Preferably, the at least one symptom is mitigated or alleviated by an increase in the trans-neuronal membrane chloride current associated with the binding of only GABA to benzodiazepine receptor complexes. Specific diseases and conditions which are affected by the modulation of one or more benzodiazepine receptors include, but are not limited to: anxiety; affective disorders such as depression, attention deficit disorder (ADD), and attention deficit disorder with hyperactivity (ADDH) or attention deficit/hyperactivity disorder (ADHD); convulsive disorders such as epilepsy; aggressive behavior; spasticity or acute muscle spasm; behavioral disorders such as mood anxiety and schizophrenia; sleep disorders such as insomnia; alcohol and drug addiction; and disorders associated with abnormal plasma hormone levels such as endocrine disorders.

As used herein, the terms "treating or preventing anxiety" and "treatment and prevention of anxiety" mean reducing the severity of symptoms associated with acute anxiety, chronic anxiety, general anxiety disorder caused by psychologic and/or physiologic factors, and other anxiety disorders such as panic disorders, mood anxiety, panic attacks, phobias, obsessive-compulsive disorders, and post traumatic distress disorder. Symptoms associated with acute anxiety include, but are not limited to, a fear of losing control of one's own actions, a sense of terror arising from no apparent reason, and a dread of catastrophe. Symptoms associated with chronic anxiety include, but are not limited to, uneasiness, nervousness, nagging uncertainty about future events, headache, fatigue, and subacute autonomic symptoms.

As used herein, the terms "treating or preventing an affective disorder" and "treatment and prevention of an affective disorder" mean reducing the severity of symptoms associated with a psychological disorder characterized by abnormality of emotional state, including but not limited to, depression, dysthymia, attention deficit disorder, attention deficit disorder with hyperactivity, bipolar disorders, bipolar and manic conditions, and the like. The terms "attention deficit disorder" (ADD) and "attention deficit disorder with hyperactivity" (ADDH), or "attention deficit/hyperactivity disorder" (AD/HD), are used herein in accordance with the accepted meanings as found in the *Diagnostic and Statistical Manual of mental Disorders,* 4$^{th}$ Ed., American Psychiatric Association (1997) (DSM-IV™).

As used herein, the terms "treating or preventing depression" and "treatment and prevention of depression" mean reducing the severity of symptoms associated with depression which include, but are not limited to, changes in mood, feelings of intense sadness, despair, mental slowing, loss of concentration, pessimistic worry, agitation, and self-deprecation. Symptoms associated with depression may also be physical symptoms, which include, but are not limited to, insomnia, anorexia, weight loss, decreased energy and libido, and abnormal hormonal circadian rhythms.

As used herein, the terms "treating or preventing a convulsive state" and "treatment and prevention of a convulsive state" mean reducing the severity and/or frequency of symptoms associated with convulsive states which include, but are not limited to, recurrent, sudden, and often brief alterations of consciousness, motor activity, sensory phenomena, and autonomic responses which are often characterized by convulsive seizures and/or tonic or clonic jerking of the extremities. The term "convulsive state" encompasses epilepsy and specific types of epileptic seizures including, but not limited to, Tonic-clonic (Grand Mal), Partial (Focal) seizures, psychomotor (Complex partial) seizures, pyknoepileptic or Absence (Petit Mal) seizure, and Myoclonic seizures.

As used herein, the terms "treating or preventing sleep disorders" and "treatment and prevention of sleep disorders" mean reducing the severity of symptoms associated with sleep disorders such as insomnia, insomnia of a primary nature with little apparent relationship to immediate somatic or psychic events, and insomnia which is secondary to some acquired pain, anxiety or depression. Symptoms associated with sleep disorders include, but are not limited to, difficulty in sleeping and disturbed sleep patterns.

As used herein, the terms "treating or preventing aggressive behavior" and "treatment and prevention of aggressive behavior" mean reducing the frequency and/or severity of manifestations of aggressive behavior which include, but are not limited to, aggressive or socially inappropriate vocal outbursts and acts of physical violence.

As used herein, the terms "treating or preventing spasticity," "treatment and prevention of spasticity," "treating or preventing spasticity and acute muscle spasm," and "treatment and prevention of spasticity and acute muscle spasm" include reducing the severity of symptoms associated with a range of abnormalities of skeletal muscle regulation that result from problems of the nervous system. A predominant symptom is heightened muscle tone or hyperexcitability of tonic stretch muscle reflexes. Symptoms of acute muscle spasm include, but are not limited to, trauma, inflammation, anxiety, and pain.

As used herein, the terms "treating or preventing a behavioral disorder" and "treatment and prevention of a behavioral disorder" mean reducing or relieving from the symptoms of a behavioral disorder, which include, but are not limited to, a subjective sense of terror, a dread of catastrophe, uneasiness, nervousness, uncertainty, headache, fatigue, disturbed thinking, inappropriate effect, auditory hallucinations, and aggressive outbursts.

As used herein, the terms "treating or preventing a schizophrenic disorder" and "treatment and prevention of a schizophrenic disorder" mean reducing the severity of symptoms associated with schizophrenic disorders. Symptoms of schizophrenic disorders include, but are not limited to, psychotic symptoms of disturbed thinking, feeling and general behavior. Specific symptoms of schizophrenic disorders include the inability to form clear, goal-directed thought, and emotional changes such as blunting and inappropriate affect. Other symptoms of schizophrenic disorders include auditory hallucinations, delusions of persecution, threats of violence, minor aggressive outbursts, aggressive behavior, disturbances of movement such as significant overactivity and excitement, and retardation and stupor.

As used herein, the terms "treating or preventing a disease associated with abnormal plasma hormone levels" and "treatment and prevention of a disease associated with abnormal plasma hormone levels" mean reducing the symptoms of diseases or conditions related to abnormal plasma levels of hormones including, but not limited to, growth hormone, ACTH, prolactin, luteinizing hormone, and other adrenocortical and testicular hormones. The term "disease associated with abnormal plasma hormone levels" encompasses endocrine disorders such as, but not limited to, growth hormone deficiency, gonadotropin deficiency, Cushing's syndrome, Grave's disease, hypothyroidism, and Addison's disease.

As used herein, the term "treating alcohol or drug addiction" means reducing the symptoms of disease or conditions related to alcohol or drug addiction including, but not limited to, drug or alcohol addiction or symptoms of withdrawal from alcohol or drugs. Symptoms of withdrawal include, but are not limited to, depression, pain, fever, restlessness, lacrimation, rhinorrhea, uncontrollable yawning, perspiration, piloerection, restless sleep, mydriasis, twitching and muscle spasms, severe aches in the back, abdomen and legs, abdominal and muscle cramps, hot and cold flashes, insomnia, nausea, vomiting, diarrhea, coryza and severe sneezing, and increases in body temperature, blood pressure, respiratory rate, and heart rate.

SYNTHESIS AND PREPARATION

Racemic N-desmethylzopiclone is readily prepared from zopiclone using an appropriate N-dealkylation reaction. Zopiclone may be prepared according to the method disclosed by U.S. Pat. Nos. 3,862,149 and 4,220,646, both of which are incorporated herein by reference. Optically pure (+) or (−) N-desmethylzopiclone can be prepared by resolution of racemic desmethylzopiclone as described herein.

One way of preparing N-desmethylzopiclone enantiomers utilizes a chiral carbonate, as outlined in Scheme 2:

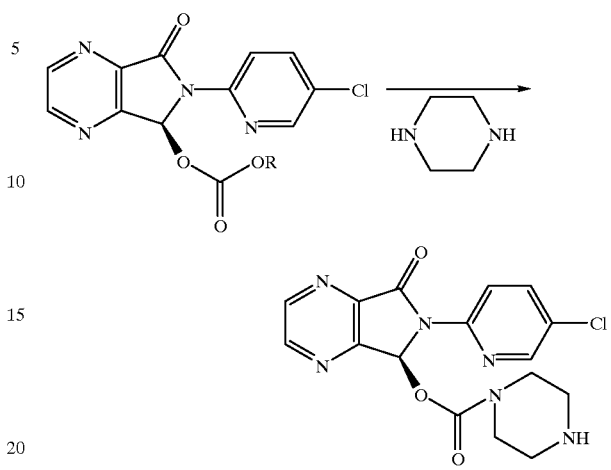

Scheme 2 wherein R is alkyl or vinyl. The carbonate can be resolved using certain lipases. Only one enantiomer can be prepared using this method, however, as the hydrolyzed chiral alcohol suffers a spontaneous racemization in the reaction medium, as shown in Scheme 3:

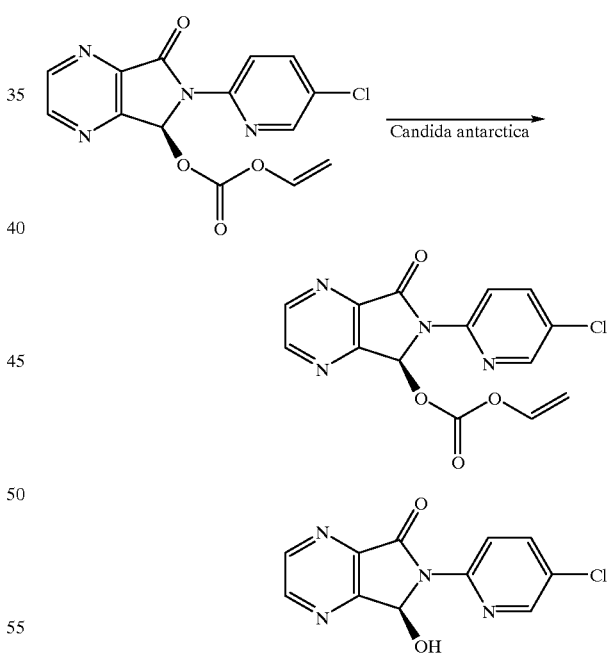

Scheme 3

It has thus been found that a more efficient method of producing optically pure enantiomers of N-desmethylzopiclone (i.e., (+)-N-desmethylzopiclone and (−)-N-desmethylzopiclone) is from zopiclone itself. Two general approaches to this method have been discovered. In the first, racemic zopiclone ((±)-zopiclone) is resolved to the desired enantiomer, and the undesired enantiomer is recycled using for example a base such as, but not limited to, DBU. This is shown in Scheme 4:

Scheme 4

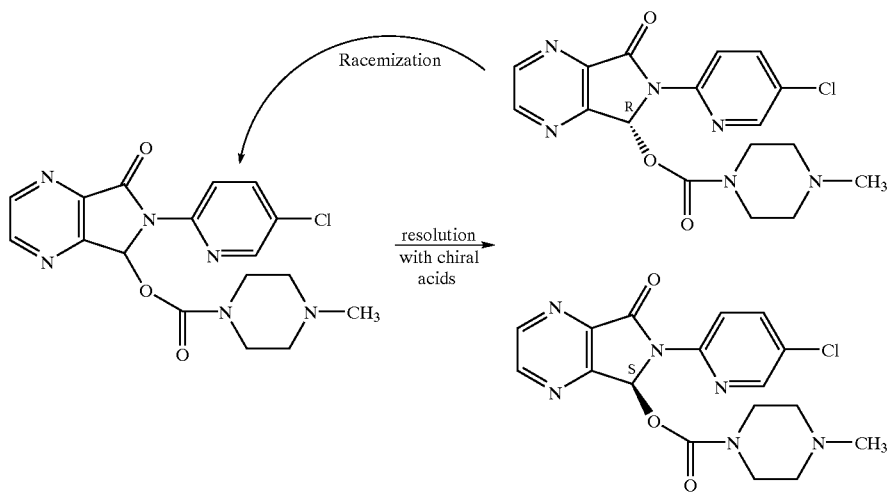

According to this approach, zopiclone is resolved using methods such as chiral chromatography, although the use of one or more chiral acids, such as malic acid, mandalic acid, and DBTA, is preferred. See, e.g., Jacques, J., et al., *Enantiomers, Racemates and Resolutions,* (Wiley-Interscience, New York, 1981); Wilen, S. H., et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E.L. Eliel, Ed. Univ. of Notre Dame Press, Notre Dame, Ind., 1972). When preparing optically pure isomers of zopiclone using these methods, Applicants have found that the resolution process is preferably performed using higher amounts of the chiral acid.

For example, this method could be used to prepare optically pure (+)-N-desmethylzopiclone, and the (−) enantiomer in the mother liquor could be racemized under basic conditions (e.g. with a tertiary amine) to reform (±)-zopiclone. However, since it has been discovered that zopiclone is not very stable under these conditions and that (±)-zopiclone is thus recovered from the undesired enantiomer in low yields, an alternative route for the recycling of the other enantiomer is outlined in Scheme 5:

Scheme 5

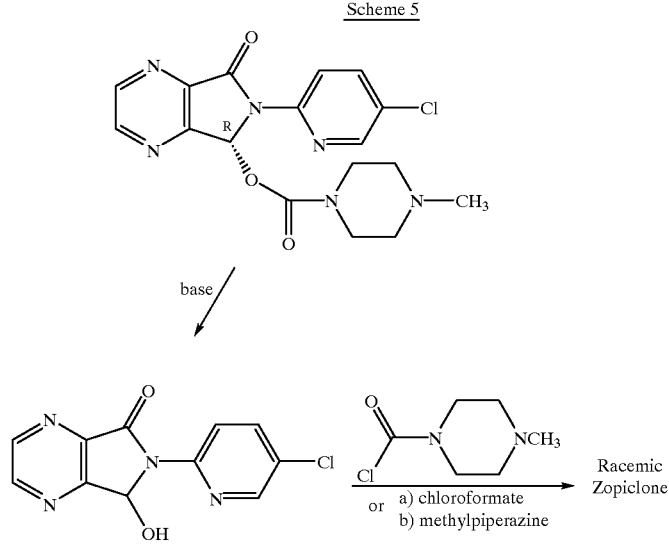

A second approach of obtaining an optically pure enantiomer of zopiclone has accordingly been developed, and is shown in Scheme 6:

Scheme 6

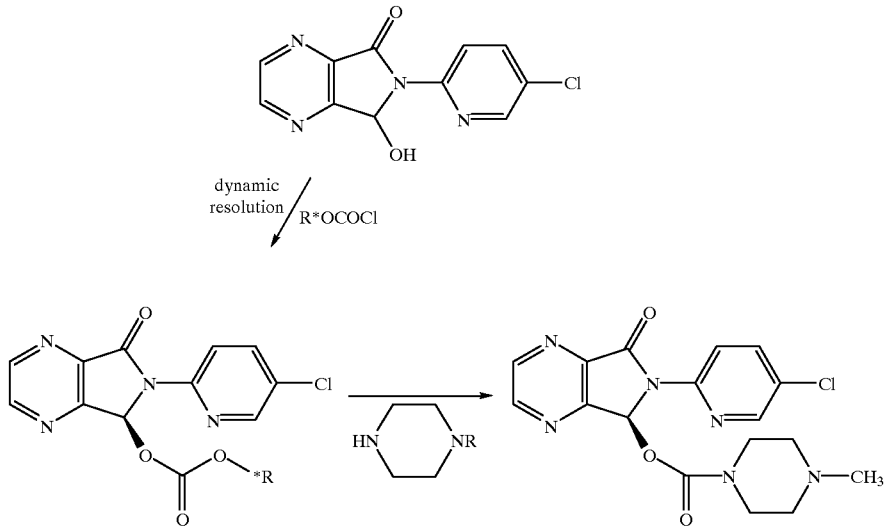

wherein R is methyl. According to this method, a commercially available alcohol precursor of zopiclone is treated with chiral auxiliary-based chloroformate to yield one major stereoisomer of the carbonate product. Referring to Scheme 6, R* is preferably a common, inexpensive chiral alcohol such as, but not limited to menthol, or a chiral aminoalcohol such as, but not limited to glycinol and aminoindanol. A particular advantage of this method is that it requires no recycling of an undesired enantiomer, yet allows recycling of the chiral auxiliary.

In another embodiment of this method, the chiral auxiliary is replaced with an enzyme as outlined in Scheme 7:

wherein R is methyl and R' is vinyl or 1-methylvinyl.

Another method useful in the production of optically pure (+)-N-desmethylzopiclone and optically pure (−)-N-desmethylzopiclone comprises the use of chloroalkyl chloroformate followed by a strong base or acid hydrolysis. See, e.g., Booher, R.N. and Pohland, A., *J. Med. Chem.* 20(8): 1065–1068 (1977). As mentioned above, however, zopiclone and N-desmethylzopiclone tend to decompose when treated with strong base or acid. Another method comprises treating zopiclone with an azodicarboxylate and hydrolyzing the resulting product under mild conditions, as shown in Scheme 8:

Scheme 7

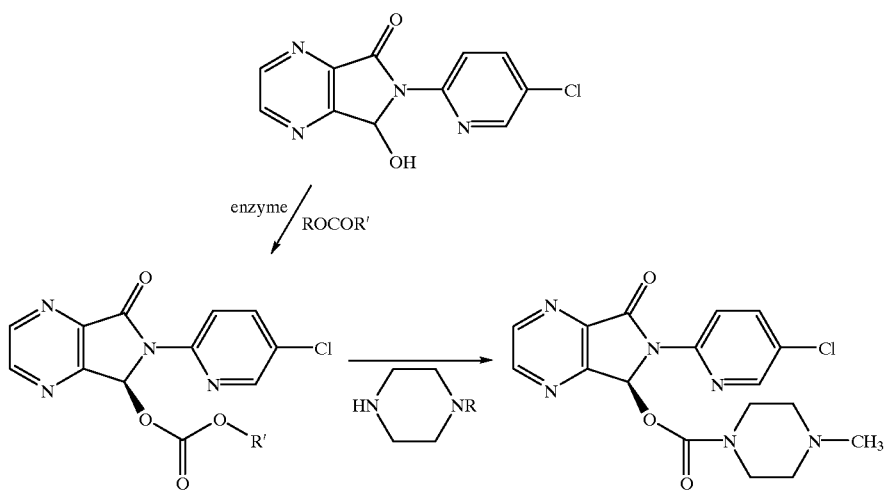

Scheme 8

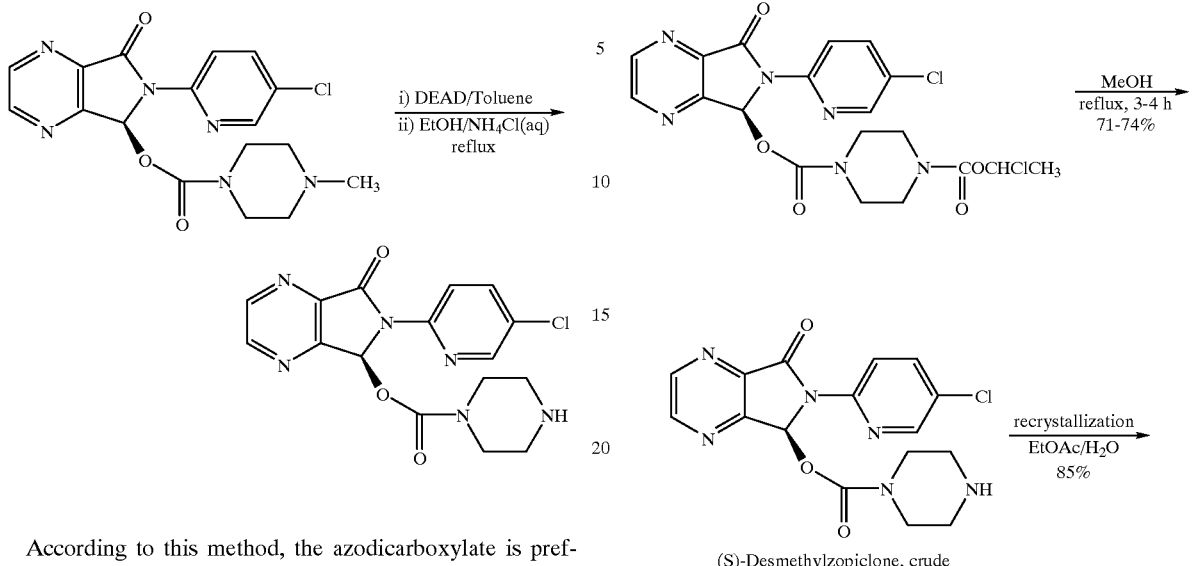

According to this method, the azodicarboxylate is preferably selected from the group consisting of diethyl azodicarboxylate, di-tert-butyl azodicarboxylate, and di-trichloromethyl azodicarboxylate. More preferably, the azodicarboxylate is diethyl azodicarboxylate or di-tert-butyl azodicarboxylate. In one embodiment, the hydrolyzing agent is a mixture of ethanol and $NH_4Cl$. Suitable solvents include toluene or other solvents of a secular nature.

A preferred method of preparing an optical isomer of N-demethylzopiclone, e.g., (S)-demethylzopiclone, is illustrated in Scheme 9.

Scheme 9

According to this method optically pure (S)-zopiclone is contacted with α-chloroethyl chloroformate in a suitable solvent such as, but not limited to, $CH_3CN$ to form the corresponding quaternary amine salt. See generally, Olofson, R. A. and Martz, T. J. *J. Org. Chem.*, 49:2081 (1984). Methanolysis of the quaternary amine salt gives the hydrochloride salt of (S)-desmethylzopiclone in high yield. The hydrochloride salt can be isolated by filtration and the reaction by-products are removed. Purification of the crude reaction product (e.g., by recrystallization) affords pure (S)-desmethylzopiclone hydrochloride.

An advantage of this process is that methanolysis releases the product as the hydrochloride salt, which precipitates out from the reaction system. The isolation is straight forward, requiring simple filtration, and al reaction by-products, including $CH_3Cl$, $CO_2$, and $CH_3CH(OMe)_2$, are volatile and easily removed during the process.

Yet another preferred method of preparing optically pure isomers of N-desmethylzopiclone, e.g., (S)-desmethylzopiclone, is shown in Scheme 10. According to this method racemic desmethylzopiclone is resolved using a suitable resolution agent such as, but not limited to, L-N-benzyloxycarbonyl phenyl alanine (L-ZPA). Racemic desmethylzopiclone can be prepared, for example, by methods disclosed in U.S. Pat. Nos. 3,862,149 and 4,220,646.

Scheme 10

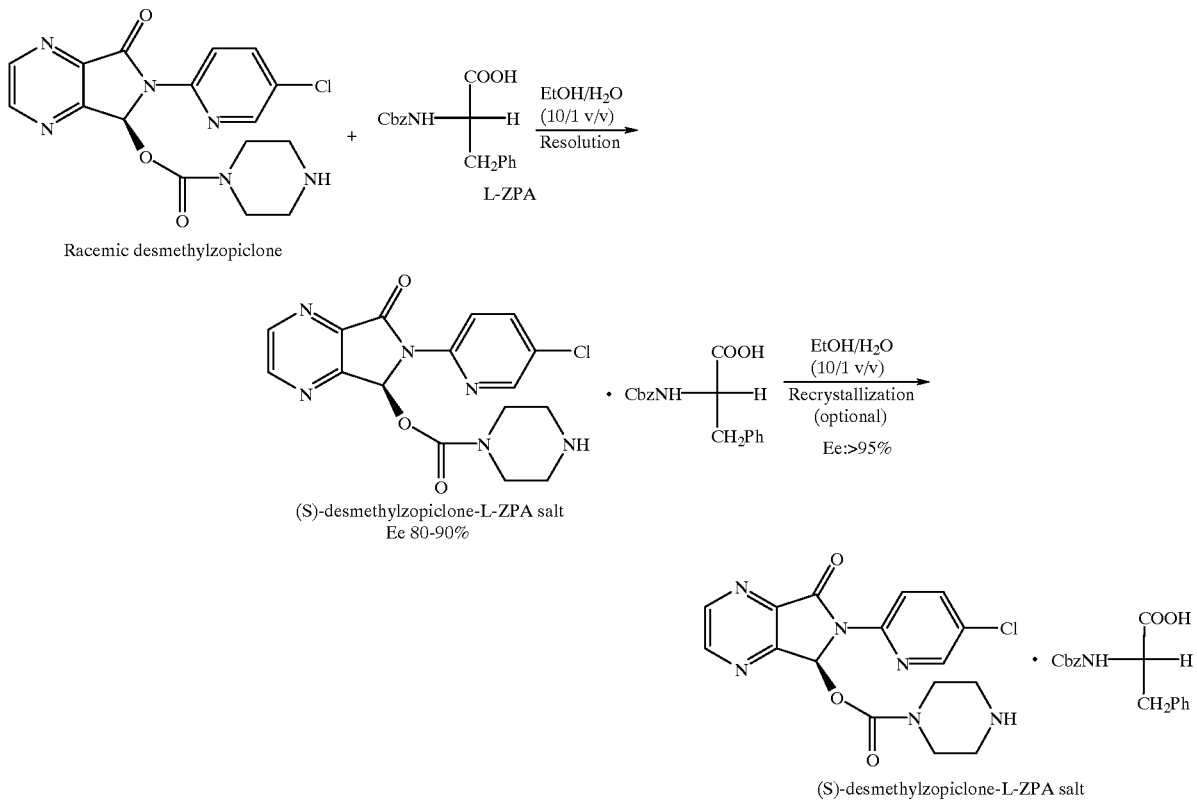

Isolation and purification of N-desmethylzopiclone is preferably done using chromatography, preferably column chromatography, and more preferably high performance liquid chromatography (HPLC). Other methods, such as isolation by evaporation of the solvent, followed by recrystallization, may also be employed.

PHARMACEUTICAL COMPOSITIONS AND METHOD OF USE

The magnitude of a prophylactic or therapeutic dose of an active ingredient of the invention (i.e., (±)-N-desmethylzopiclone, optically pure (+)-N-desmethylzopiclone, and optically pure (+)-N-desmethylzopiclone) in the acute or chronic management of the diseases or conditions recited herein will vary with the nature and severity of the disease or condition.

The magnitude of a prophylactic or therapeutic dose of an active ingredient of the invention (i.e., (±)-N-desmethylzopiclone, optically pure (+)-N-desmethylzopiclone, or optically pure (−)-N-desmethylzopiclone) will also vary according to the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 0.1 mg to about 500 mg per day, given as a single once-a-day dose, or as divided doses from 2 to 4 times throughout the day. Preferably, a daily dose range should be from about 0.5 mg to about 250 mg per day, more preferably, between about 1 mg and about 200 mg per day. In managing the patient, the therapy should be initiated at a lower dose, perhaps about 0.1 mg to about 25 mg, and increased if necessary up to about 1 mg to about 200 mg per day as either a single dose or divided doses, depending on the patient's global response.

It may be necessary to use dosages of the active ingredient outside the ranges disclosed herein in some cases, as will be apparent to those of ordinary skill in the art. Because elimination of zopiclone metabolites from the bloodstream is dependant on renal and liver function, it is recommended that the total daily dose be reduced by at least about 50% in patients with moderate hepatic impairment, and that it be reduced by about 25% in patients with mild to moderate renal impairment. For patients undergoing hemodialysis, it is recommended that the total daily dose be reduced by about 5% and that the dose be withheld until the dialysis treatment is completed. Furthermore, it is noted that the clinician or treating physician will know how and when to interrupt, adjust, or terminate therapy in conjunction with individual patient response.

The phrase "therapeutically effective amount" as used herein with respect to the treatment or prevention of diseases and conditions encompasses the above described dosage amounts and dose frequency schedules. Different therapeutically effective amounts may be applicable for different diseases and conditions, as will be readily known by those of ordinary skill in the art. Similarly, amounts sufficient to treat or prevent such disorders, but insufficient to cause adverse effects associated with zopiclone, are also encompassed by the above described dosage amounts and dose frequency schedules.

Any suitable route of administration may be employed for providing the patient with an effective dosage of racemic or optically pure (+)- or (−)-N-desmethylzopiclone. Suitable routes include, but are not limited to, oral, mucosal (e.g., nasal, sublingual, vaginal, buccal or rectal), parenteral (e.g., subcutaneous, intravenous, bolus injection, intramuscular, or intraarterial), , transdermal, and.

The pharmaceutical compositions of the invention comprise N-desmethylzopiclone, or a pharmaceutically acceptable salt, solvate, hydrate, or clathrate thereof as an active ingredient, and may also contain a pharmaceutically acceptable carrier and optionally other therapeutic ingredients known to those skilled in the art. Preferred pharmaceutical compositions comprise optically pure (+)-N-desmethylzopiclone, or a pharmaceutically acceptable salt, solvate, hydrate, or clathrate thereof.

Compositions of the invention are suitable for oral, mucosal (e.g., nasal, vaginal, or rectal), parenteral (e.g., subcutaneous, intravenous, bolus injection, intramuscular, or intraarterial), sublingual, transdermal, or buccal administration, although the most suitable route in any given case will depend on the nature and severity of the condition being treated. The compositions may be conveniently presented in unit dosage form and prepared by any of the methods well known in the part of pharmacy. Dosage forms include tablets, caplets, troches, lozenges, dispersions, suspensions, suppositories, solutions, capsules, soft elastic gelatin capsules, patches, and the like. Preferred dosage forms are suitable for oral administration.

In practical use, racemic or optically pure (+)- or (−)-N-desmethylzopiclone can be combined as the active ingredient in intimate admixture with a pharmaceutically acceptable carrier according to conventional pharmaceutical compounding techniques. The carrier may take a wide variety of forms and comprises a number of components depending on the form of preparation desired for administration. The compositions of the invention include, but are not limited to, suspensions, solutions and elixirs; aerosols; or excipients, including, but not limited to, starches, sugars, microcrystalline cellulose, diluents, granulating agents, lubricants, binders, disintegrating agents, and the like. Preferably, the pharmaceutical composition is in the form of an oral preparation.

Pharmaceutical compositions of the invention suitable for oral administration may be presented as discrete pharmaceutical unit dosage forms, such as capsules, cachets, soft elastic gelatin capsules, tablets, caplets, or aerosols sprays, each containing a predetermined amount of the active ingredients, as a powder or granules, or as a solution or a suspension in an aqueous liquid, a non-aqueous liquid, an oil-in-water emulsion, or a water-in-oil liquid emulsion. Such compositions may be prepared by any method known in the art of pharmacy which comprises the step of bringing an active ingredient into association with a carrier. In general, the compositions are prepared by uniformly and intimately admixing the active ingredients with liquid carriers or finely divided solid carriers or both, and then, if necessary, shaping the product into the desired presentation. Oral solid preparations are preferred over oral liquid preparations. Preferred oral solid preparations are capsules and tablets.

A tablet may be prepared by compression or molding techniques. Compressed tablets may be prepared by compressing in a suitable machine the active ingredient in a free-flowing form, such as powder or granules, optionally mixed with one or more pharmaceutically acceptable excipients, such as a binder, lubricant, inert diluent, granulating agent, surface active or dispersing agent, or the like. Molded tablets may be made by molding, in a suitable machine, a mixture of the powdered compound moistened with an inert liquid diluent. Preferably, each tablet, cachet, caplet, or capsule contains from about 0.1 mg to 500 mg, more preferably from about 0.5 mg to about 250 mg, and most preferably between about 1 mg and about 200 mg.

Pharmaceutical compositions of the invention may also be formulated as a pharmaceutical composition in a soft elastic gelatin capsule unit dosage form by using conventional methods well known in the art. See, e.g., Ebert, *Pharm. Tech,* 1(5):44–50 (1977). Soft elastic gelatin capsules have a soft, globular gelatin shell somewhat thicker than that of hard gelatin capsules, wherein a gelatin is plasticized by the addition of plasticizing agent, e.g., glycerin, sorbitol, or a similar polyol. The hardness of the capsule shell may be changed by varying the type of gelatin used and the amounts of plasticizer and water. The soft gelatin shells may contain a preservative, such as methyl- and propylparabens and sorbic acid, to prevent the growth of fungi. The active ingredient may be dissolved or suspended in a liquid vehicle or carrier, such as vegetable or mineral oils, glycols, such as polyethylene glycol and propylene glycol, triglycerides, surfactants, such as polysorbates, or a combination thereof.

A pharmaceutically acceptable excipient used in the compositions and dosage form of the invention may be a binder, a filler, or a mixture thereof. A pharmaceutically acceptable excipient may also include a lubricant, a disintegrant, or mixtures thereof. One embodiment of the invention encompasses a pharmaceutical composition which is substantially free of all mono- or di-saccharide excipients. Another embodiment encompasses a pharmaceutical composition which is free of lactose.

Binders suitable for use in the compositions and dosage forms of the invention include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, or mixtures thereof.

Suitable forms of microcrystalline cellulose include, for example, the materials sold as AVICEL-PH-101, AVICEL-PH-103 and AVICEL-PH-105 (available from FMC Corporation, American Viscose Division, Avicel Sales, Marcus Hook, Pa., U.S.A.). An exemplary suitable binder is a mixture of microcrystalline cellulose and sodium carboxymethyl cellulose sold as AVICEL RC-581 by FMC Corporation.

Fillers suitable for use in the compositions and dosage forms of the invention include, but are not limited to, talc, calcium carbonate (e.g., granules or powder), lactose, microcrystalline cellulose, powdered cellulose, dextrates, kaolin, mannitol, silicic acid, sorbitol, starch, pre-gelatinized starch, or mixtures thereof.

The binder/filler in pharmaceutical compositions of the invention is typically present in about 50 to about 99 weight percent of the pharmaceutical composition.

Disintegrants are used to cause the tablet to disintegrate when exposed to an aqueous environment. Too much of a disintegrant will produce tablets which may disintegrate in the bottle due to atmospheric moisture; too little may be insufficient for disintegration to occur and may thus alter the rate and extent of release of the drug ingredient(s) from the dosage form. Thus, a sufficient amount of disintegrant that is neither too little nor too much to detrimentally alter the release of the drug ingredient(s) should be used to form dosage forms of racemic and optically pure (+)- or (−)-N-desmethylzopiclone made according to the invention. The amount of disintegrant used varies based upon the type of formulation and mode of administration, and is readily discernible to those of ordinary skill in the art. Typically, about 0.5 to about 15 weight percent of disintegrant, preferably about 1 to about 5 weight percent of disintegrant, may be used in the pharmaceutical composition.

Disintegrants suitable for use in the compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants suitable for use in the compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, or mixtures thereof. Additional lubricants include, for example, a syloid silica gel (AEROSIL 200, manufactured by W.R. Grace Co. of Baltimore Md.), a coagulated aerosol of synthetic silica (marketed by Deaussa Co. of Plano, Tex.), CAB-O-SIL (a pyrogenic silicon dioxide product sold by Cabot Co. of Boston, Mass.), or mixtures thereof. A lubricant may optionally be added, typically in an amount of less than about 1 weight percent of the pharmaceutical composition.

In addition to the common dosage forms set out above, the compounds of the invention may also be administered by controlled release means or delivery devices that are well known to those of ordinary skill in the art, such as those described in U.S. Pat. Nos.: 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, the disclosures of which are each incorporated herein by express reference thereto. These pharmaceutical compositions can be used to provide slow or controlled-release of one or more of the active ingredients therein using, for example, hydropropylmethyl cellulose, other polymer matrices, gels, permeable-membranes, osmotic systems, multilayer coatings, microparticles, liposomes, microspheres, or the like, or a combination thereof to provide the desired release profile in varying proportions. Suitable controlled-release formulations known to those of ordinary skill in the art, including those described herein, may be readily selected for use with the pharmaceutical compositions of the invention. Thus, single unit dosage forms suitable for oral administration, such as tablets, capsules, gelcaps, caplets, and the like, that are adapted for controlled-release are encompassed by the invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations may include: 1) extended activity of the drug; 2) reduced dosage frequency; and 3) increased patient compliance. In addition, controlled-release formulations can be used to effect the time of onset of action or other characteristics, such as blood levels of the drug, and thus may affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

The controlled-release of an active ingredient may be stimulated by various inducers, for example pH, temperature, enzymes, water, or other physiological conditions or compounds. The term "controlled-release component" in the context of the invention is defined herein as a compound or compounds, including, but not limited to, polymers, polymer matrices, gels, permeable membranes, liposomes, microspheres, or the like, or a combination thereof, that facilitates the controlled-release of the active ingredient.

Pharmaceutical compositions of the invention may also be formulated for parenteral administration by injection (e.g., subcutaneous, intravenous, bolus injection, intramuscular, or intraarterial), and may be dispensed in a unit dosage form, such as a multidose container or an ampule. Such compositions for parenteral administration may be in the form of suspensions, solutions, emulsions, or the like in aqueous-or oily vehicles, and in addition to the active ingredients may contain one or more formulary agents, such as dispersing agents, suspending agents, stabilizing agents, preservatives, and the like.

The invention is further defined by reference to the following examples describing in detail the preparation of the compositions of the invention. It will be apparent to those skilled in the art that many modifications, both to materials and methods, may be practiced without departing from the purpose and interest of this invention.

EXAMPLES

Synthesis of N-desmethylzopiclone

Racemic and optically pure enantiomers of N-desmethylzopiclone were prepared according to the procedures provided below. It should be noted that X-ray crystal diffraction studies indicate that the absolute configuration of both (+)-zopiclone and (+)-N-desmethylzopiclone is the S-configuration.

Example 1

Synthesis of (±)-N-desmethylzopiclone

To a solution of (±)zopiclone (6.2 g, 20 mmol) in toluene (120 ml) was added diethyl azodicarboxylate (DEAD, 8.2 g, 50.0 mmol) and the solution was stirred at 60° C. for 26 hours. The solvent was removed under reduced pressure. The residue was added to 60 ml of EtOH/NH$_4$Cl aq (1:1) and the resulting mixture was refluxed for 4 hours. The reaction mixture was concentrated to remove ethanol under reduced pressure and the residue was partitioned by adding saturated NaHCO$_3$ solution and CH$_2$Cl$_2$ (100 ml). The organic phase was then separated and washed with water (30 ml), brine (30 ml), and dried over Na$_2$SO$_4$. The crude product was loaded onto a silica gel column and eluted with CH₃CN:MeOH:NH₄OH (25:4:1) to give 1.56 g of product with chemical purity of approximately 91% (25% yield). A second flash chromatography yielded (±)-N-desmethylzopiclone with >98% chemical purity. $^1$H NMR (CDCl₃), δ: 2.4–3.8 (b, 8H), 7.7–7.82 (dd, 1H), 8.0 (s, 1H), 8.4 (s,1H), 8.5 (d, 1H), 8.82–8.88 (dd, 2H), 2–6 (NH). $^{13}$C NMR δ45.5, 45.9, 79.3, 116.3, 128.5, 138.3, 144.1, 146.9, 148.0, 153.7, 155.8, 163.2.

Example 2

Synthesis of (+)-zopiclone (a) Preparation of (+)-zopiclone-D-malate salt:

A three-neck 2.0 L flask was charged with (±)-zopiclone (40 g, 0.101 mol, 1.0 eq), D-malic acid (13.4 g, 0.97 eq.), 406 mL MeOH and 754 mL acetone. The reaction mixture was heated in an oil bath to 55–56 ° C. for about 30 min and gradually cooled to 45–47 ° C. over approximately 30 mn. (+)-zopiclone-D-malate seeds (0.1g, 0.02%) was added at 45–47°C. The reaction mixture was cooled to 40° C. over 1 h and then cooled to 10–15° C. over 3 h. Then the slurry was held at 10–15° C. for 30 min. The solid product was isolated by filtration and washed with cold MeOH (2×50 mL, 0–5° C.). The white product was dried at 30–40° C./28 mmHg over 6–12 h to give (+)-Zopiclone-D-malate (22.6 g, 42 %, 96.5 % ee).

(b) Preparation of (+)-zopiclone:

A three-neck 250 mL flask was charged with (+)-zopiclone-D-malate (10 g, 93% ee), 20 mL water and 150 mL of EtOAc. The reaction mixture was heated in an oil bath to 30–40° C. An aqueous K₂CO₃ solution (40%, 8 g) was added slowly over 5 min. The mixture was then heated to 60–65° C. and the organic phase was isolated and washed with 100 mL water. The mixture was polish filtered, rinsed with EtOAc (20 mL) and concentrated to 70–80 mL. The resulting slurry was cooled and held for 2 h at 0–5 ° C. The crystal product was isolated by filtration and was washed with cold EtOAc (20 mL, 0–5 ° C.). The white product was dried at 30–40° C./28 mmHg over 6–12 h to give (+)-zopiclone (6.4 g, 86.2%, 99.9% ee).

Example 3

Synthesis of (+)-N-desmethylzopiclone

To a solution of (+)-zopiclone (4.0 g, 10.3 mmol) in toluene (100 ml) was added DEAD (5.4 g, 30.0 mmol) and the solution was stirred at 55° C. for 40 hours. The solvent was removed under reduced pressure and the residue was added 60 ml of EtOH/NH₄Cl aq (1:1) and the resulting mixture was refluxed for 4 hours. The reaction mixture was concentrated under reduced pressure to remove the ethanol and the residue was partitioned by adding saturated NaHCO₃ solution and CH₂C 1₂ (100 ml). The organic phase was then washed with water (30ml), brine (30 ml), and dried over Na₂SO₄. The crude product was loaded onto a silica gel column and eluted with CH₃CN:MeOH:NH₄OH (25:4: 1) to give 1.25 g of the product with chemical purity of ca 90% (27% yield). A second flash chromatography yielded (+)-N-desmethylzopiclone with >97% chemical purity and >99% ee by chiral HPLC: Chiralcel OD, mobile phase: Hexane:Ethanol:Methanol:DEA (55:15:30:0.1). Retention time: 11.6 minutes for the (+) isomer and 14.7 minutes for (−) isomer. ([α]=+141 C=1, CDCl₃), $^1$H NMR (CDCl₃), δ2.4–3.8 (b, 8H), 7.7–7.82(dd, 1H), 8.0 (s, 1H), 8.4 (s, 1H), 8.5 (d, 1H), 8.82–8.88 (dd, 2H), 2–6 (NH). $^{13}$C NMR δ: 45.5, 45.9, 79.3, 116.3, 128.5, 138.3, 144.1, 146.9, 148.0, 153.7, 155.8, 163.2.

Example 4

Synthesis of (−)-N-desmethylzopiclone (−)-Desmethylzopiclone was prepared from (−)-zopiclone according to the procedure described above. ([α]=−158, C=1, CDl₃), $^1$H NMR (CDCl₃), δ: 2.4–3.8 (b, 8H), 7.7–7.82 (dd, 1H), 8.0 (s, 1H), 8.4 (s, 1H), 8.5 (d, 1H), 8.82–8.88 (dd, 2H), 2–6 (NH). $^{13}$C NMR, δ: 45.5, 45.9, 79.3, 116.3, 128.5, 138.3, 144.1, 146.9, 148.0, 153.7, 155.8, 163.2.

Example 5

Preparation of (+)-desmethylzopiclone hydrochloride (a) Demethylation:

To a 12 L reaction flask under Ar, were charged (+)-zopiclone (778 g, 2.0 mmol), ACN (4L) and 1-chloroethyl chloroformate (328.9 g, 2.3 mol). The reaction mixture was heated at 73–75° C. for 6 h with stirring. MeOH (1.0 L) was added and the mixture was 10 heated under a reflux for 3–4 h. The reaction slurry was cooled to 5–10° C. for 2 h. The solid product was isolated via filtration, followed by washing with EtOH (200 mL×3) and toluene (200 mL×3). The final product was dried in an oven for 12 h (28 mm Hg) at 40–45° C. The isolated product (i.e., crude (+)-desmethylzopiclone hydrochloride salt) was 610 g (74%).

(b) Recrystallization of (+)-desmethylzopiclone hydrochloride (DMZ):

To a 12 L reaction flask equipped with overhead stirrer under argon, were charged crude (+)-DMZ.HCl salt (450 g), EtOH (4.8 L) and water (1.5 L). The reaction mixture was heated under reflux for 1 h, and then cooled to 20° C. over 1 h. The resulting slurry was 20 further cooled to 0–5° C. and stirred at that temperature for 1 h. The white solid product was isolated by filtration followed by washing with EtOH (500 mL). The final product was dried in an oven for 12 h (28 mm Hg) at 40–45° C. The isolated product was 377 g (84%). $^{1H\ NMR}$ (300 MHZ, DMSO), δ (ppm): 8.95 (dd, 2H, J =7.2, 3.0 Hz),), 8.57 (d, 1H, J=7.2 Hz), 8.45 (s, 1H), 8.10 (s, 1H), 7.80 (m, 1H), 3.60 (bro d, 2H), 3.25 (bro s, 2H), 2.88 (bro s, 2H), 2.62 (bro s, 2H). MS 374 (M+).

The process was repeated and the results from both experiments are summarized in Table 1 below.

TABLE 1

|  | Demethylation[1] | | Recrystallization[2] | |
| --- | --- | --- | --- | --- |
| Experiment | Yield (%) | HPLC A % | Yield (%) | Purity (HPLC assay %) |
| 1 | 610 g(74) | 99.74 | 377 g(84) | 99.5 |
| 2 | 580 g(71) | 99.34 | 485 g(86) | 99.5 |

[1]Using (+)-zopiclone (ee>99%) prepared in accordance with Example 2.
[2]Partial crude product was used for the recrystallization Example 6

Resolution of racemic desmethylzopiclone

This is an alternate method of preparing of optically pure (+)-desmethylzopiclone. Racemic desmethylzopiclone can be obtained either by the chloroformate demethylation method described in Example 5 above using racemic zopiclone as the starting material, or by known literature methods.

(a) Identifying Resolution Agents:

A reagent screen was performed to identify an effective resolution agent for racemic N-desmethylzopiclone. The screen identified L-N-benzyloxycarbonyl phenyl alanine (L-ZPA) (available from SEM chemical) as an effective resolution agent for desmethylzopiclone and indicated that other acids suitable for resolution of zopiclone are ineffective for the resolution of N-desmethylzopiclone. L-ZPA may also be used for the resolution of racemic zopiclone. Table 2 summarizes the experimental results.

TABLE 2

| Exp. # | (±)-Desmethyl-zopiclone (g) | Acid (g) | Solvents | Conditions | Comments and Yields |
|---|---|---|---|---|---|
| 1 | 1.0 | L-ZPA 0.8(1 eq.) | 40 70 mL EtOH/7 mL water | 1. 75–79° C. 1 h 2. rt. for 2 h | 80% ee, 33% yield |
| 2 | 10 | L-ZPA 30.8(1 eq.) | EtOH/water | 1. 75–79° C. 1 h 2. rt. for 4 h | 80% ee, 28% yield |
| 3 | 8.0 | L-ZPA 6.15(1 eq.) | EtOH/water | 1. 75–79° C. 1 h 2. rt. for 12 h | 91% ee, 31.4% yield |
| 4 | 1.0 | D-malic acid 0.36(1 eq.) | 20 mL EtOH/2 mL water | 1. 75–79° C. 1 h 2. rt. for 14 h | No crystals observed. |
| 5 | 1.0 | D-malic acid 0.36(1 eq.) | 20 mL MeOH/2 mL water | 1. 75–79° C. 1 h 2. rt. for 12 h | No crystals observed. |
| 6 | 1.0 | D-DTTA 1.0(1 eq.) | 50 mL EtOH/5 mL water | 1. 75–79° C. 1 h 2. rt. for 2 h | 1. at room with 80% ee. 2. Hold it for 1 h, 0% ee. |
| 7 | 1.0 | D-DTTA 1.0(1 eq.) | 50 mL EtOH/5 mL water | 1. 75–79° C. 1 h 2. 79° C. for 5 min. | Filtered at 50° C. with 15% yield and 95.5% ee. |
| 8 | 32 | L-ZPA 1.0 eq. | 1600 mL EtOH/160 mL water | 1. 75–79° C. 1 h 2. rt. for 14 h 3. reslurry in EtOH | 27.6% yield, 96% ee |

Using L-ZPA, and a solvent mixture of EtOH and water highly optically enriched (typical >90% ee) (+)-desmethylzopiclone.L-ZPA salt was isolated. The free base of (+)-desmethylzopiclone can be obtained by the treatment of (+)-desmethylzopiclone.L-ZPA salt in EtOAc with $K_2CO_3$ solution.

(b) Resolution of (±)-Desmethylzopiclone:

(±)-Desmethylzopiclone (8.0 g, 21.3 mmol) and 6.4 g L-ZPA (21.3, 1 equiv.) were combined in 40 mL water and 400 mL EtOH. The mixture was heated to 75–78° C. for 1 h to form a clear solution. The mixture was cooled to 20° C. overnight. The solids were isolated and the cake was washed with 150 mL EtOH. The wet cake was transferred into a 500 mL flask with 150 mL EtOH. The slurry was refluxed for 2 h. The slurry was cooled to 0–5° C. for 1 h. The solid product was isolated via filtration and was washed with EtOH (25 mL). The final product was dried in an oven for 12 h (28 mm Hg) at 45–50° C. to give (+)-desmethylzopiclone-L-ZPA salt (4.5 g, 31.4%, 91% ee).

Example 7
Determination of biological activity

A pharmacologic study is conducted to determine the relative potency, comparative efficacy, and binding affinity of N-desmethylzopiclone. The pharmacologic profile of hypnotic-sedative, anxiolytic agents of the benzodiazepine class is well established, and has been extended to non-benzodiazepine agents of the cyclopyrrolone class. See, e.g., Goodman & Gilman's The Pharmacological Basis of Therapeutics, Hardman, J. G., et al., eds. ch. 17, pp. 361–396 (9[1]h ed., 1996); Bardone, M. C., et al., Abstract No. 2319, 7th Int. Congr. Pharm. Paris, (July, 1978: Pergamon Press, London); Julou, L. et al, Pharmacology, Biochemistry and Behavior, 23:653–659 (1985).

A variety of experimental models can be used to characterize the various activities of N-desmethylzopiclone, including its anticonvulsant, myorelaxant, anti-aggressive, sedative-hypnotic, and anxiolytic (i.e., anti-anxiety) activities. In an examination of each element of the pharmacologic profile, N-desmethylzopiclone is compared with pharmacologic standards such as nitrazepam and diazepam in a variety of animal models. The dose (mg/kg) of each agent that is capable of inhibiting by 50% (the $ID_{50}$ or $ED_{50}$) an induced response in rodents, for example, provides the basis for comparison. Pentylenetetrazole-induced, picrotoxin convulsions, and electrically-induced convulsions can thus be used to demonstrate the anti-convulsant activity of N-desmethylzopiclone. Haefely, W., Psychotropic Agents, Hofmeister, F. and Stille, G., eds., part 11, pp. 12–262 (Springer Verlag, Berlin: 1981). Further, in the rat, in the amygdala kindled model of epilepsy, daily electrical stimulation of the amygdala induces a progressive increase of epileptic after discharge duration, with increasing epileptic behavioral symptoms, producing in about two weeks a generalized convulsive crisis. Presumably, previously ineffective stimuli have sensitized neuronal pathways, and it has been suggested that a similar mechanism may exist for the induction of an anxiety state in man after repeated stresses.

Similar models are available for determination of the myorelaxant, anti-aggressive, and sedative-hypnotic activities of N-desmethylzopiclone in both mice and rats. See, Julou, L. et al., Pharmacology, Biochemistry and Behavior, 23:653–659 (1985).

The pharmacologic activity of N-desmethylzopiclone may also be compared with benzodiazepines for its affinity for binding to both CNS and peripheral benzodiazepine receptors. In this biochemical affinity binding study, the binding of $^3$H-radiolabeled N-desmethylzopiclone is studied in a synaptosomal membrane preparation of cerebral tissue from female rat brain. The tissue is preferably prepared by homogenization in ice-cold isosmotic (0.32 M) sucrose, and centrifugation, first at low speed (1,000×g for 10 minutes), with the resultant supernatant solution then being centrifuged at high speed (48,000×g for 20 minutes). The resulting pellet is suspended in Kreb-Tris buffer at pH 7.4, and the concentration of protein is adjusted to 15 mg/ml. This synaptosomal membrane preparation may be stored at −18° C. until used at room temperature (e.g., about 22° C.) with the radio-cyclopyrrolone in Kreb-Tris buffer solution pH 7.4. Following a 30-minute incubation, separation of the bound and free drug is performed by centrifugation at 1,000×g for 10 minutes in scintillation vials. The supernatant solution is collected, the pellet is dissolved in a counting vehicle, and the radioactivity is counted using a liquid scintillation counter. The original supernatant solution from the first incubation, which contains unbound radiolabeled drug, may be used in additional binding studies using the same method. Additional controls involve, for instance, study of the radioactivity bound in the presence of 10 $\mu$M flunitrazepam (a benzodiazepine), which experiment is useful in assessing non-specific binding. Furthermore, the binding of various concentrations of radiolabeled N-desmethylzopiclone in the presence of a fixed concentration of GABA provides additional information as to the modulation of the GABA-ergic system by N-desmethylzopiclone. See, Jacqmin, P., et al, *Arch. Int. Pharmacodyn*, 282:26–32 (1986); Jacqmin, P., etal., *J. Pharm. Belg.* 40:35–54 (1985). With regard to peripheral benzodiazepine receptors and their distinction from central benzodiazepine binding sites, see, e.g., Verma, A. and Snyder, S. H., *Ann. Rev. Pharmacol. Toxicol.* 29:307–322 (1989), which is hereby incorporated by reference.

Example 8

Measured biological activity

The binding of N-desmethylzopiclone was determined at the central benzodiazepine receptor and at the non-selective muscarinic receptor, both of which were isolated from rat cerebral cortex. Compounds were tested initially at 10 $\mu$M in duplicate, and if at least a 50% inhibition of specific binding was observed, they were tested further at 10 different concentrations in duplicate in order to obtain full competition curves. $IC_{50}$ values (concentration required to inhibit 50% specific binding) were determined by nonlinear regression analysis of the curves, and inhibition constants ($K_i$) were also calculated. These data are provided below in Table 3.

TABLE 3

| Compound | Benzodiazepine $IC_{50}$ and ($K_i$) Values (nM) | Muscarinic (% Inhibition) |
|---|---|---|
| (±)-N-desmethylzopiclone | 1,100 (924) | 10 |
| (+)-N-desmethylzopiclone | 545 (458) | 19 |
| (−)-N-desmethylzopiclone | 7,090 (5,960) | 24 |
| Diazepam | 12 (10) | not determined |

Racemic and optically pure enantiomers of N-desmethylzopiclone clearly have affinity for the benzodiazepine site. Advantageously, and as discussed above, these compounds exhibited little activity at the muscarinic receptor.

Example 9

Oral formulation

Suitable ingredients of a tablet dosage form of (+)-N-desmethylzopiclone are provided in Table 4.

TABLE 4

| Component | Quantity per Tablet (mg) |
|---|---|
| (+)-N-desmethylzopiclone | 75 |
| Lactose | 125 |
| Corn Starch | 5.0 |
| Water (per thousand tablets) | 30.0 ml* |
| Magnesium Stearate | 0.5 |

*The water evaporates during manufacture.

The active ingredient (i.e., (+)-N-desmethylzopiclone) is blended with the lactose until a uniform blend is formed. The smaller quantity of corn starch is blended with a suitable quantity of water to form a corn starch paste. This is then mixed with the uniform blend until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration. Tablets may be coated by standard aqueous or nonaqueous techniques.

Another tablet dosage formulation suitable for use with an active ingredient of the invention is provided by Table 5:

TABLE 5

| | Quantity per Tablet (mg) | | |
|---|---|---|---|
| Component | Formula A | Formula B | Formula C |
| (+)-N-desmethylzopiclone | 20 | 40 | 100 |
| Lactose BP | 134.5 | 114.5 | 309.0 |
| Starch BP | 30 | 30 | 60 |
| Pregelatinized Maize Starch BP | 15 | 15 | 30 |
| Magnesium Stearate | 0.5 | 0.5 | 1.0 |
| Compression Weight | 200 | 200 | 500 |

The active ingredient is sieved and blended with lactose, starch, and pregelatinized maize starch. Suitable volumes of purified water are added and the powders are granulated. After drying, the granules are screened and blended with the magnesium stearate. The granules are then compressed into tablets using punches.

Tablets of other strengths may be prepared by altering the ratio of active ingredient to pharmaceutically acceptable carrier, the compression weight, or by using different punches.

Example 10

Oral formulation

Capsules of (±)-N-desmethylzopiclone may be made using the ingredients provided in Table 6:

TABLE 6

| Capsule Unit Dosage Forms | | | |
|---|---|---|---|
| | Quantity per Capsule (mg) | | |
| Formulation | A | B | C |
| (±)-N-desmethylzopiclone | 50.0 | 100.0 | 200.0 |
| Lactose | 48.5 | 148.5 | 48.5 |
| Titanium Dioxide | 0.5 | 0.5 | 0.5 |
| Magnesium Stearate | 1.0 | 1.0 | 1.0 |
| Fill Weight | 100.0 | 250.0 | 250.0 |

The active ingredient (i.e., (±)-N-desmethylzopiclone) is sieved and blended with the excipients. The mixture is filled into suitably sized two-piece hard gelatin capsules using suitable machinery. Other doses may be prepared by altering the ratio of the active ingredient (e.g., (±)-N-desmethylzopiclone) and pharmaceutically acceptable carrier, the fill weight and, if necessary, by changing the capsule size to suit.

Example 11

Oral Formulation

Hard gelatin capsules of (+)-N-desmethylzopiclone may be made using the ingredients provided in Table 7:

TABLE 7

Hard Gelatin Capsule Unit Dosage Forms

| Component | 0.1 mg capsule (amount in mg) | 5 mg capsule (amount in mg) | 20 mg capsule (amount in mg) |
| --- | --- | --- | --- |
| (±)-N-desmethylzopiclone | 0.1 | 5.0 | 20.0 |
| Microcrystalline Cellulose | 90.0 | 90.0 | 90.0 |
| Pre-gelatinized Starch | 102.7 | 97.8 | 82.8 |
| Croscarimellose | 7.0 | 7.0 | 7.0 |
| Magnesium Stearate | 0.2 | 0.2 | 0.2 |

The active ingredient is sieved and blended with the excipients listed. The mixture is filled into suitably sized two-piece hard gelatin capsules using suitable machinery and methods well known in the art. See, e.g., Remington's Pharmaceutical Sciences, 16th or 18th Editions, each incorporated herein. Other doses may be prepared by altering the fill weight and, if necessary, changing the capsule size to suit. Any of the stable, non-lactose hard gelatin capsule formulations above may be formed.

Example 12

Oral formulation

Compressed tablet formulations of (±)-N-desmethylzopiclone may be made using the ingredients provided in Table 8:

TABLE 8

Compressed Tablet Formulations

| Component | 0.1 mg capsule (amount in mg) | 5 mg tablet (amount in mg) | 20 mg tablet (amount in mg) |
| --- | --- | --- | --- |
| (±)-N-desmethylzopiclone | 0.1 | 5.0 | 20.0 |
| Microcrystalline Cellulose | 90.0 | 90.0 | 90.0 |
| Pregelatinized Starch | 102.7 | 97.8 | 82.8 |
| Croscarmellose | 7.0 | 7.0 | 7.0 |
| Magnesium Stearate | 0.2 | 0.2 | 0.2 |

TABLE 8-continued

The active ingredient is sieved through a suitable sieve and blended with the non-lactose excipients until a uniform blend is formed. The dry blend is screened and blended with the magnesium stearate. The resulting powder blend is then compressed into tablets of desired shape and size. Tablets of other strengths may be prepared by altering the ratio of the active ingredient (i.e., (±)-N-desmethylzopiclone) to the excipient(s) or modifying the tablet weight.

The embodiments of the invention described above are intended to be merely exemplary, and those skilled in the art will recognize, or be able to ascertain using no more than routine experimentation, numerous equivalents to the specific procedures described herein. All such equivalents are considered to be within the scope of the invention and are encompassed by the following claims.

What is claimed is:

1. A method of treating or preventing alcohol or drug addiction in a patient, which comprises administering to a patient suffering from alcohol or drug addiction a therapeutically or prophylactically effective amount of N-desmethylzopiclone, or a pharmaceutically acceptable salt, solvate, hydrate, or clathrate thereof.

2. The method of claim 1 wherein the N-desmethylzopiclone is racemic.

3. The method of claim 1 wherein the N-desmethylzopiclone is (+)-N-desmethylzopiclone, substantially free of its (−) enantiomer.

4. The method of claim 1 wherein the N-desmethylzopiclone is (−)-N-desmethylzopiclone, substantially free of its (+) enantiomer.

5. The method of claim 1 wherein the therapeutically or prophylactically effective amount of N-desmethylzopiclone or pharmaceutically acceptable salt, solvate, hydrate, or clathrate thereof is from about 0.1 mg to about 500 mg.

* * * * *